United States Patent [19]

Morgan

[11] Patent Number: 5,024,221
[45] Date of Patent: Jun. 18, 1991

[54] PROGRAMMABLE BAND-PASS AMPLIFIER FOR USE WITH IMPLANTABLE MEDICAL DEVICE

[75] Inventor: Wayne A. Morgan, Granada Hills, Calif.

[73] Assignee: Siemens-Pacesetter, Inc., Sylmar, Calif.

[21] Appl. No.: 121,547

[22] Filed: Nov. 17, 1987

Related U.S. Application Data

[63] Continuation-in-part of Ser. No. 735,251, May 17, 1985, abandoned.

[51] Int. Cl.$^5$ ............................................... A61N 1/00
[52] U.S. Cl. ............................... 128/419 PG; 128/903
[58] Field of Search ................ 128/419 PG, 903, 904, 128/696, 700; 330/9

[56] References Cited

U.S. PATENT DOCUMENTS

| | | | |
|---|---|---|---|
| 4,261,369 | 4/1981 | Allor | 128/696 |
| 4,306,198 | 12/1981 | Okada | 330/260 |
| 4,320,347 | 3/1982 | Haque | 330/9 |
| 4,342,001 | 7/1982 | Sauer | 330/9 |
| 4,381,786 | 5/1983 | Duggan | 128/419 PG |
| 4,429,281 | 1/1984 | Ito et al. | 330/9 |
| 4,436,093 | 3/1984 | Belt | 128/419 PG |
| 4,502,019 | 2/1985 | Van Roermund | 330/261 |
| 4,521,743 | 6/1985 | Heimer | 330/296 |
| 4,531,106 | 7/1985 | Ganesan | 333/173 |
| 4,549,548 | 10/1985 | Wittkampf et al. | 128/419 PG |
| 4,555,668 | 11/1985 | Gregorian et al. | 330/9 |
| 4,617,481 | 10/1986 | Masuda | 307/491 |

OTHER PUBLICATIONS

Duffin et al., "A 24 Channel Electrocardiographic Preamplifier," Proceedings of the 23rd ACEMB, Nov. 15–19, 1970.

*Primary Examiner*—Francis Jaworski
*Assistant Examiner*—George Manuel
*Attorney, Agent, or Firm*—Bryant R. Gold; Malcolm J. Romano; Lisa P. Weinberg

[57] ABSTRACT

A switched-capacitor, band-pass, programmable amplifier is used as a sense amplifier in an implantable cardiac pacemaker. Switching means are used to switchably connect various capacitors to the same amplifier circuits. Clock generator means are used to generate clock signals that are used to control the rate at which the switching means operates. By programmably selecting the switching rate to be a desired value, the band-pass characteristics and gain of the sense amplifier may be varied. When a pacemaker stimulation pulse occurs, the band-pass characteristics and/or gain of the sense amplifier, may also be automatically varied to improve amplifier recovery time. The rate at which the capacitors are switchably connected to the amplifier circuits, may be selected remotely, thereby allowing the band-pass characteristics to be programmable.

14 Claims, 6 Drawing Sheets

PROGRAMMABLE BAND-PASS AMPLIFIER FOR USE WITH IMPLANTABLE MEDICAL DEVICE

This application is a continuation-in-part of Application Ser. No. 735,251, filed May 17, 1985, now abandoned.

This invention relates to implantable medical devices, and more particularly to a switched-capacitor, programmable, band-pass amplifier suitable for use in implanted devices, such as cardiac pacemakers. The invention offers the capability of being able to put all of the frequency-determining elements of a sense amplifier within a single integrated circuit.

Switched-capacitor amplifier theory is explained in IEEE Journal of Solid-State Circuits, Vol. SC-12, No. 6, pp. 242-249, December 1977, and in Vol. SC-14, No. 6, December 1979, commencing at page 1034, and in the references cited at the end of those articles. Reference is made to such articles as part of the prior art to this invention.

The present invention is particularly useful in implanted devices and is most useful as a sensing amplifier in implanted pacemakers. In sensing the electrical activity of the heart, a high impedance sensing amplifier responsive to the frequency band of the P-wave and the R-wave (QRS complex) is utilized. It is desired that frequencies below and above the frequency band associated with P-waves and R-waves be rejected; or, at least, be amplified less than the desired frequency band. A suitable frequency band for a sense amplifier of an implanted pacemaker would be about 30-90 Hz. That is, the lower frequency gain roll off begins at a lower cut-off frequency of about 30 Hz and is down 12 db per octave below 30 Hz. Similarly, the high or upper end of the band might be at an upper cut-off frequency of about 90 Hz with gain roll off down 12 db per octave above 70 Hz. Other bands may be selected, as may other high or low frequencies and rate of roll off. The ones mentioned are believed to be optimum and include the necessary frequencies to sense P-waves and R-waves and to reject the low-frequency T-waves (below 10 Hz) and higher frequency myocardial waves (on the order of 100 Hz or more).

When a device, such as a pacemaker is implanted, it is usually necessary to set its "threshold" (gain) to fit the particular implantation. It may also be desirable to change its band-pass characteristics. ("Band-pass characteristics", as used herein, relate to the upper and lower cut-off frequencies of the frequency band amplified by a particular amplifier, the upper cut-off frequency representing the high end of the band, and the lower cut-off frequency representing the low end of the band.) The subject invention provides greater flexibility to accommodate particular implantations as well as changes occurring after implantation. Variations in placement of the leads, as well as other factors, such as fibrosis, movement of lead after implantation, and other physiological changes in the patient, can all cause variations in the strength of the signals sensed. A significant factor affecting signal strength is the location of the electrodes of the lead in the heart (e.g., whether it has penetrated the myocardium or is merely touching the endocardial tissue, as is commonly desired for optimum signal).

Sometimes, it may be desirable to momentarily change the band-pass frequencies or the gain of the sensing amplifier during delivery of a pacemaker stimulation pulse. Such action advantageously minimizes the recovery time of the amplifier and thus improves its capability.

Advantageously, the gain or the band-pass frequency, or both, of the band-pass amplifier of the present invention may be programmed by electrical signals. Consequently, where such an amplifier is used within a pacemaker having telemetry features, it is possible to program the subject band-pass amplifier from outside the patient's body. Thus, the threshold (gain) of the amplifier may be programmed from outside the patient's body as may the band-pass frequency range.

SUMMARY OF THE INVENTION

It is an object of the present invention to provide a programmable, band-pass amplifier for use in an implantable medical device, such as a pacemaker.

It is a further object of this invention to provide an implantable amplifier which is programmable as to gain and as to frequency response, or both, from outside the body.

Another object of the invention is to provide a band-pass amplifier which can be constructed within a single integrated circuit.

Still another object of this invention is to provide a band-pass amplifier for use as a sense amplifier in an implantable pacemaker which has variable band-pass characteristics and wherein its band-pass characteristics can be changed in synchrony with other events associated with the operation of the pacemaker, such as the generation of stimulation pulses.

To these and other ends, the present invention relates to an implantable, programmable medical device that includes a programmable implantable medical device comprising a pair of electrodes for sensing electrical signals developed therebetween; programmable band-pass amplifier means coupled to the electrodes for sensing and processing electrical signals, the programmable band-pass amplifier means including an amplifier having an input terminal and an output terminal, the electrical signals sensed by the electrodes being applied to the input terminal, the amplifier causing the electrical signals to be amplified by a desired gain factor and presented at the output terminal of the amplifier, at least one capacitor, switching means for switchably coupling the at least one capacitor to the amplifier, the switching means limiting the electrical signals amplified by the gain factor to those having a frequency that falls within a band of frequencies bound by a lower cut-off frequency and an upper cut-off frequency, the upper and lower cut-off frequencies of the frequency band being controlled by the rate at which the at least one capacitor is switchably coupled to the amplifier by the switching means, the switching rate, in turn, being controlled by a clock signal applied to the switching means; clock signal generating means for generating the clock signal at one of a plurality of possible clock frequencies; and telemetry means for remotely selecting the clock frequency of the clock signal generating means; whereby the frequency band of the band-pass amplifier can be changed to a desired value by remotely changing the frequency of the clock signal generated by the clock signal generating means.

Further, the invention is directed to a programmable band-pass sense amplifier that can be used within an implantable medical device that includes a pair of electrodes, the sense amplifier comprising a sensing amplifier for use in an implantable medical device, the implantable medical device including a pair of electrodes between which an electrical signal having a broad frequency spectrum may be developed, the sensing amplifier comprising a first capacitor; first amplifier means coupled to the pair of electrodes for amplifying selected frequency components of the electrical signal developed between the pair of electrodes, the selected frequency components comprising those components of the electrical signal having a frequency less than a first specified frequency, the first specified frequency being determined by the rate at which the first capacitor is switchably connected to the first amplifier means; clock generating means for generating first and second clock signals; first switching means responsive to the first clock signal for switchably connecting the first capacitor to the first amplifier means at a first switching rate derived from the first clock signal, whereby the first clock signal comprises a first control parameter that defines the first specified frequency; a second capacitor; second amplifier means coupled to the pair of electrodes, the selected frequency components comprising those components of the electrical signal having a frequency greater than a second specified frequency, the second specified frequency being determined by the rate at which the second capacitor is switchably connected to the second amplifier means; second switching means responsive to the second clock signal for switchably connecting the second capacitor to the second amplifier means at a second switching rate derived from the second clock signal, whereby the second clock signal comprises a second control parameter that defines the second specified frequency; and means for serially connecting the first and second amplifier means, whereby only those frequency components of the electrical signal developed between the pair of electrodes above the second specified frequency and below the first specified frequency are amplified by the serial combination of the first and second amplifier means.

Further objects and features will become more apparent from the following drawings and description.

DETAILED DESCRIPTION OF THE INVENTION

The following description is of the best presently contemplated mode of carrying out the invention. This description is not to be taken in a limiting sense, but is made merely for the purpose of describing the general principles of the invention. The scope of the invention should be determined with reference to the appended claims.

Many of the details associated with the operation of an implantable cardiac pacemaker can be found in U.S. Pat. Nos. 4,232,679; 4,559,947; and 4,686,988; which patents are incorporated herein by reference.

Figure 1:
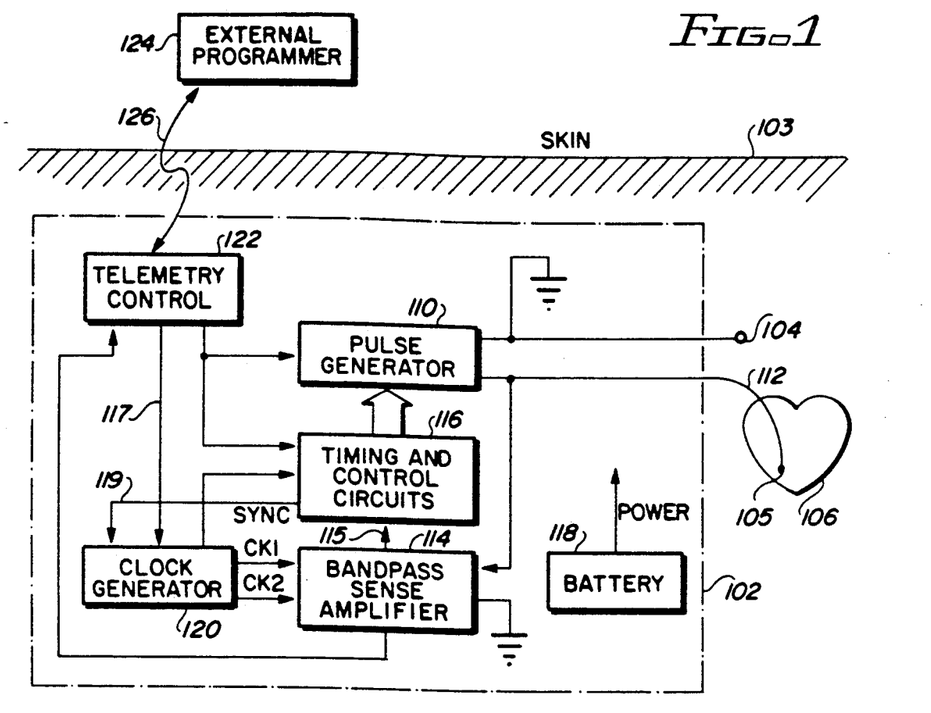
FIG. 1 is a block diagram of an implantable pacemaker that utilizes the programmable band-pass sense amplifier of the present invention.

Referring to FIG. 1, the present invention comprises an implantable medical device 102, such as a pacemaker, that may be implanted beneath the skin 103 of a patient. The implantable medical device 102 has associated therewith a pair of electrodes 104, 105 which are used to sense electrical signals developed between the electrodes within the patient's body. In the embodiment shown in FIG. 1, the implantable medical device 102 comprises a cardiac pacemaker. Thus, one of the electrodes 105 is in contact with the patient's heart 106, and the other electrode 104 is positioned in a desired location so that electrical signals develop between the electrodes 104 and 105 can be adequately sensed. Typically, the electrode 104 will be part of the case of the medical device 102 (a unipolar operation). In other embodiments, the electrode 104 may also be positioned within the heart 106 (bipolar operation).

The pacemaker included within the implantable medical device 102 includes a pulse generator 110 for generating stimulation pulses that may be delivered to the heart 106 by way of a pacemaker lead 112, at the distal end of which is located the electrode 105. For purposes of the present invention, the pulse generator 110 is of conventional design.

The conductive portion of the pacemaker lead 112 is also electrically connected to a band-pass sense amplifier 114. When a signal is sensed by the sense amplifier 114 that is determined to be either a P-wave or an R-wave, the sense amplifier signals the timing and control circuits 116 over signal line 115 that such P-wave or R-wave has been sensed. In response to this signal, the timing and control circuits reset the pacemaker's escape interval, at the end of which the pulse generator 110 would generate a stimulation pulse. If no natural cardiac activity is sensed during the escape interval, then the pulse generator 110 provides a stimulation pulse to the heart 106, as above-described. In this manner, the pulse generator 110 only provides a stimulation pulse to the heart 106 in the absence of a naturally occurring heartbeat, thereby preserving the limited energy stored within a battery 118 of the device 102.

As will be explained in more detail hereinafter, a clock generator circuit 120 provides a plurality of clock signals, ck 1 and ck 2, to the band-pass sense amplifier 114. These two clock signals control the rate at which various capacitors are switchably coupled to the sense amplifier 114. In turn, the rate at which these capacitors are switchably coupled to sense amplifier 114 determines the band-pass characteristics of the sense amplifier 114.

Advantageously, the rate of the clock signals ck 1 and ck 2 is selected by means of control signals generated by telemetry control circuitry 122. In turn, telemetry control circuitry 122 is controlled remotely by means of an external programmer 124 that communicates with the telemetry control circuitry 122 by way of a transmitted signal 126.

Those skilled in the art will appreciate that the above description of an implanted pacemaker is greatly simplified. In particular, the telemetry control circuitry 122 contains many elements used to realize the function described above, including reception circuits, decoding circuits, memory circuits, and the like. However, for purposes of the invention herein described, the telemetry control circuitry 122 is of conventional design and generates appropriate control signals that select the frequency or rate of the clock signals ck 1 and ck 2 that are generated by the clock generator 120. In turn, this selection can be controlled through use of external programmer 124. Details associated with the operation of the pacemaker circuits can be found in the above-referenced patents.

Referring next to FIGS. 2-9, the details associated with the band-pass sense amplifier 114 and the clock generator 120 will be described.

Figure 2A:
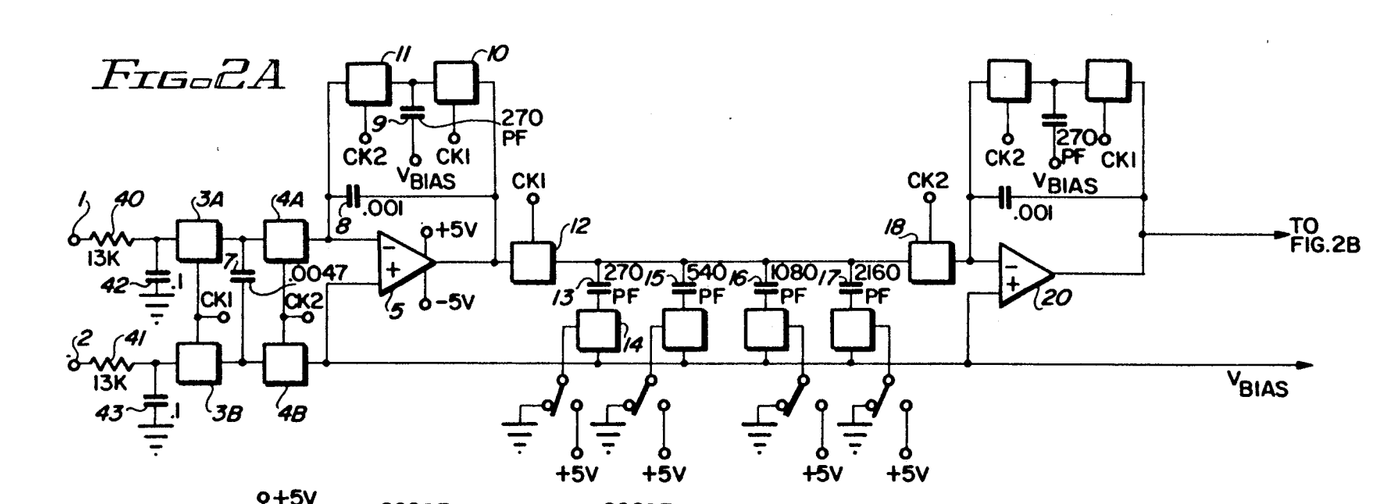
FIG. 2A is a schematic diagram of the low-pass sections of the band-pass sense amplifier.

In FIG. 2A, the electrical input to the sensing amplifier 114 is shown as being double-ended. This allows receiving both positive- and negative-going signals such as from a bipolar type lead (one having two electrodes). Amplifier 5 (a high-impedance, operational amplifier such as a commercially available CD 3240) is an input amplifier which comprises (with associated circuitry) a low-pass stage and which converts the differential input to a single-ended output.

In FIG. 2A, at the front end of the amplifier, there is an anti-aliasing filter. This filter is an analog or R-C type filter which substantially reduces any frequency above ½ of the clock frequency—in this case, above 1000 Hz. Therefore, the anti-aliasing filter reduces frequencies above 1000 Hz to below the lowest amplitude that is expected to be detected by the amplifier. It is expected that the filter would assure that any frequency above 1000 Hz would be much less than half a millivolt, because it is expected that the amplifier would be detecting threshold signals down to half a millivolt. The resistors 40 and 41 and capacitors 42 and 43 provide such a low-pass, anti-aliasing filter. The capacitors 42 and 43 attenuate any frequencies above 1000 Hz.

Switches 3A and 3B, under the control of clock 1 phase (ck 1), first connect input capacitor 7 to receive the input signal on leads 1 and 2. Switches 4A and 4B, under the control of clock 2 phase (ck 2), next connect input capacitor 7 to transfer its charge to the input of amplifier 5. At this time, switches 3A and 3B are open so that the input impedance presented to amplifier 5 is substantially only that of the capacitor 7. This can be accomplished by having ck 1 and ck 2 non-overlapping, as shown in the timing diagram included in FIG. 4B. (Ck 1 and ck 2 are generated by the clock generation circuitry 120, shown in FIG. 4A.)

The output of amplifier 5 is fed back to the input through capacitor 8 and switched capacitor 9. Feedback switch 10, operated by ck 1, acts to charge capacitor 9, and feed back switch 11, operated by ck 2, acts to transfer the charge to the input of amplifier 5.

It is known in the electronic art (see, e.g., the IEEE articles referenced above) that a switched capacitor exhibits an equivalent resistance of $(1/\text{frequency}) \times (1/\text{capacitance})$. Thus, input capacitor 7 provides an effective input resistance and capacitor 9 provides an effective resistance across 8, forming an R-C feedback circuit. This R-C combination determines the frequency responses of the amplifier and together with the input capacitance 7 (which looks like a resistance when switched rapidly) configures the amplifier 5 into a low-pass stage (defining the gain roll off at the upper end of the band-pass). Thus, the capacitance values and the frequency at which capacitor 9 is switched between input and output determine the filter response of this low-pass section. The gain is determined by the ratio of the input capacitance 7 to the feedback capacitance 9. For example, if input capacitance 7 is 0.0047 microfarads, and feedback capacitance is 270 picofarads, the gain is approximately 17.4.

In the low-pass section of the sense amplifier 114 (FIG. 2A), it is desired that frequencies below 90 Hz be passed. At a clock frequency of 2 kHz, a capacitor 9 of 270 pf provides an equivalent resistance of 1.85 megohms. A resistance of 1.85 megohms connected in parallel with a capacitance of 0.001 microfarads (capacitor 8) gives a pole frequency of approximately 565 radians per second, which is 90 Hz.

The next stage of the amplifier 114 shown in FIG. 2A is also a low-pass stage comprising amplifier 20 (which may, like amplifier 5, be a CD 3240) which may well use the same component values as the first stage, and has the same frequency response. The gain, however, may be programmed by switching in or out the capacitors 13, 15, 16, and 17 by means of switches such as switch 14. Such switches are controlled by, for example, another switch, a data bus, a flip-flop, etc., or other means which is programmable as desired in the particular case. The capacitors 13, 15 16, and 17 are related, each succeeding capacitor being twice the value of the prior one. If the input capacitance to amplifier 20 is 270 pf (capacitor 13 only), then the gain of that stage would be 1 (270/270).

If the values are, for example, 270 pf (capacitor 13), 540 pf (capacitor 15), 0.0011 mfd (capacitor 16), and 0.0022 mfd (capacitor 17), then the gain can be programmed in this stage to be 0, 1, 2, 3, 4, etc., in increments up to 10.

Figure 2B:
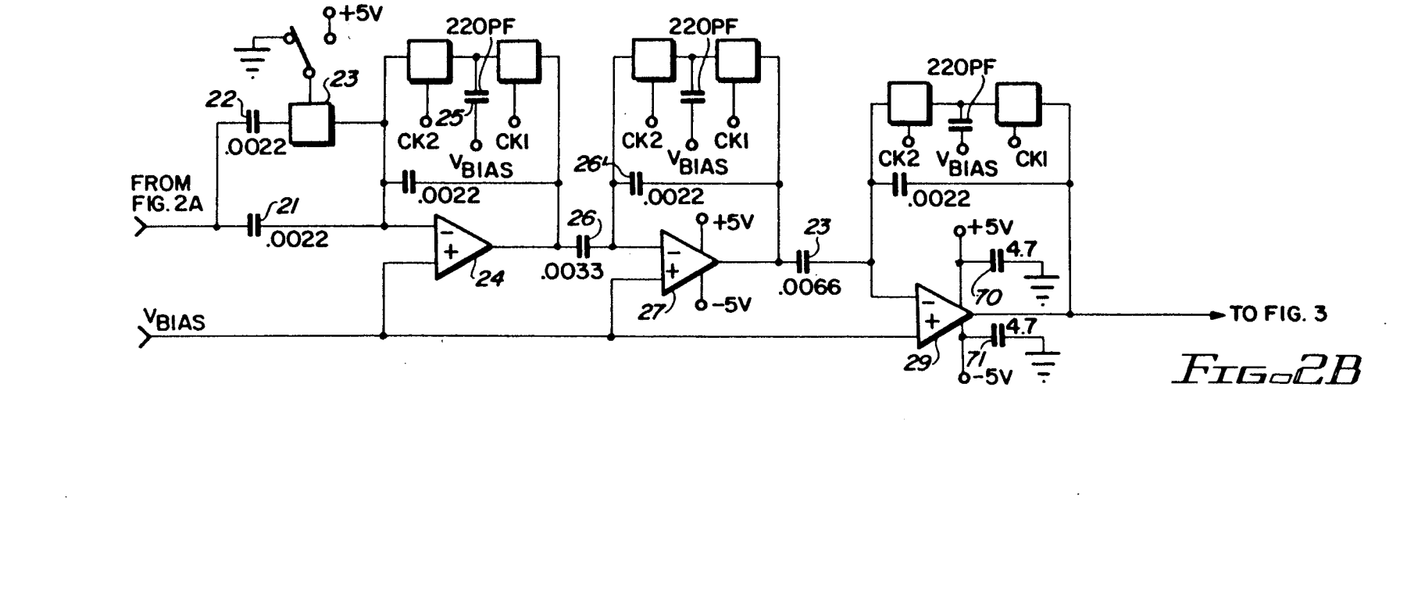
FIG. 2B is a schematic diagram of the high-pass sections of the band-pass sense amplifier.

FIG. 2B shows the high-pass section of the sense amplifier 114, designed to pass frequencies above approximately 30 Hz. In this stage, amplifier 24 has an input capacitor 21 (and capacitor 22 in parallel within capacitor 21 if switch 23 is closed) to provide a high-pass section. The feedback circuit is identical to the prior two stages, except capacitor 25 is 220 pf, and thus the roll off commences at 32 Hz at 6 db per octave. Gain can be increased from 1 to 2 by switch 23 adding capacitor 22.

The next stage of the high-pass section, also shown in FIG. 2B, is similar; however, the input capacitance 26 is larger, therefore the gain through amplifier 27 is greater. For example, if capacitor 26 is 0.0033 mfd, the gain would be 1.5, assuming a feedback capacitor 26' of 0.0022 mfd. The final stage of the high-pass section has an input capacitor 28 of 0.0066 mfd and the feedback circuit is the same as the prior high-pass stages. Therefore, the gain of this stage is 3. The 5-volt inputs to amplifier 29 are connected to filter capacitors 70 and 71 which smooth out any spikes or transients which may appear across the power source. All of the amplifiers 24, 27, and 29 may, like the previous amplifiers, be realized from commercially available operational amplifiers, or chips, such as the CD 3240's.

Returning to FIG. 1 for the moment, one feature of the present invention allows a rate change of the clock signals ck 1 and ck 2 to be synchronized with the Occurrence of a prescribed event, such as the generation of a stimulation pulse. A sync pulse, generated by the timing and control circuits 116 in convention manner, is generated so as to begin concurrent with the timing out of the appropriate escape interval of the pacemaker. This sync pulse is directed to the clock generator 120 over signal line 119. Clock generator 120, in turn, changes the rate of the ck 1 signal and the ck 2 signal during the time that the sync pulse is high.

Figure 3:
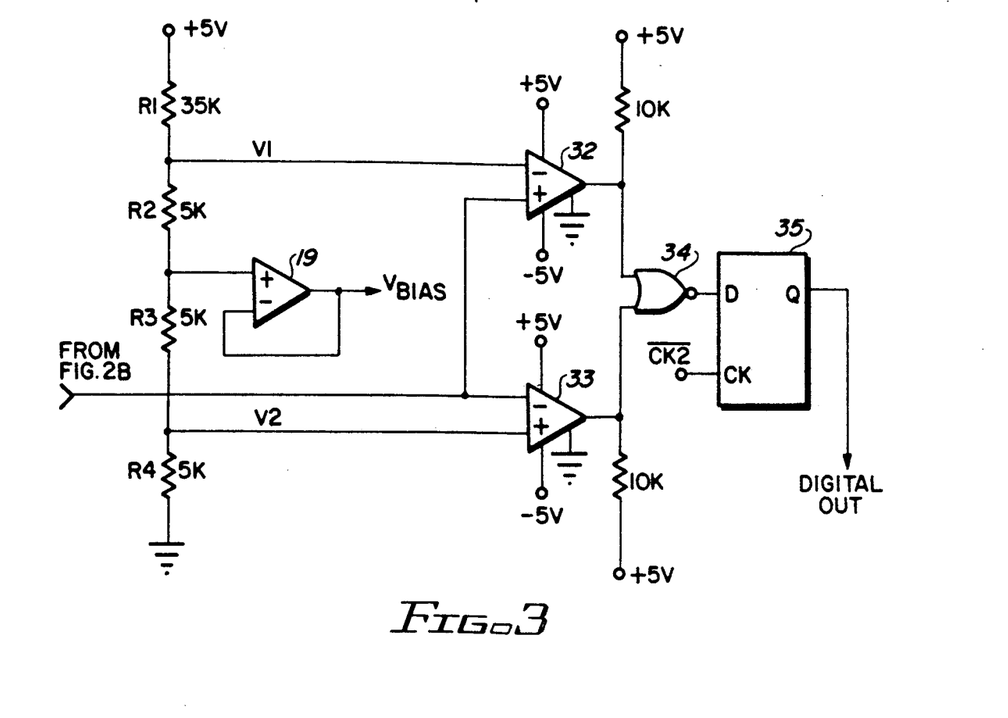
FIG. 3 is a schematic diagram of a window comparator circuit (a detector of signals exceeding a selected positive or negative amplitude) used in conjunction with the amplifier of FIGS. 2A and 2B.

The output signal of amplifier 29 is fed to a window comparator circuit which is set forth in FIG. 3. Amplifiers 32 and 33 are connected to provide detection of positive and negative signals which exceed certain threshold levels. These levels are generated by a resistor dividing network compression resistors R1, R2, R3, and R4. If the output signal (from FIG. 2B) is greater than a first level, V1, say, 1½ volts, or less than a second level, V2, say ½ volt, the output signal from FIG. 2B causes amplifiers 32 or 33 to assume a first voltage level that passes through NOR gate 34 to D flip-flop 35, which flip-flop is clocked by 1 or ck 2, may be used, but the trailing edge (the falling edge of a positive clock signal or the rising edge of a negative clock signal) should be used in order to allow the output of NOR gate 34 to settle down before setting the flip-flop 35. Thus, it is seen that flip-flop 35 assumes one state if the band-passed signal from FIG. 2B falls within the "window" defined by the first and second threshold levels, and assumes another state if the signal falls out of the window, either on the upper or lower side thereof. Any output signal (from FIG. 2B) that is greater than a desired level, either positive or negative, will set the flip-flop 35. Regulator amplifier 19 provides a V-bias voltage to various feedback capacitors of the system and sets the operating point of the amplifiers 24, 27, and 29 (FIG. 2B).

Figure 4A:
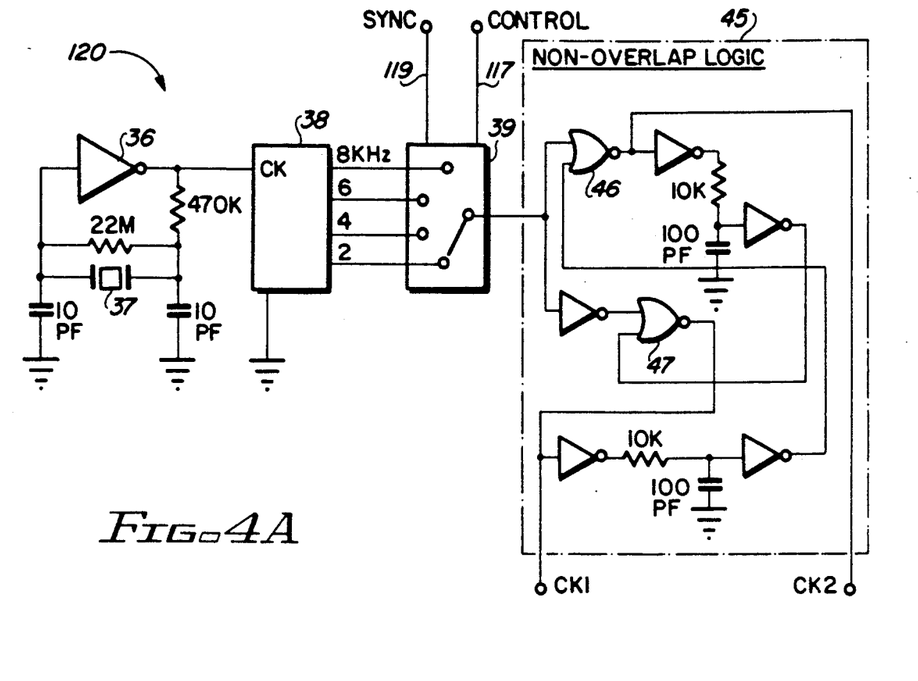
FIG. 4A is a schematic diagram of the clock generation circuits.
Figure 4B:
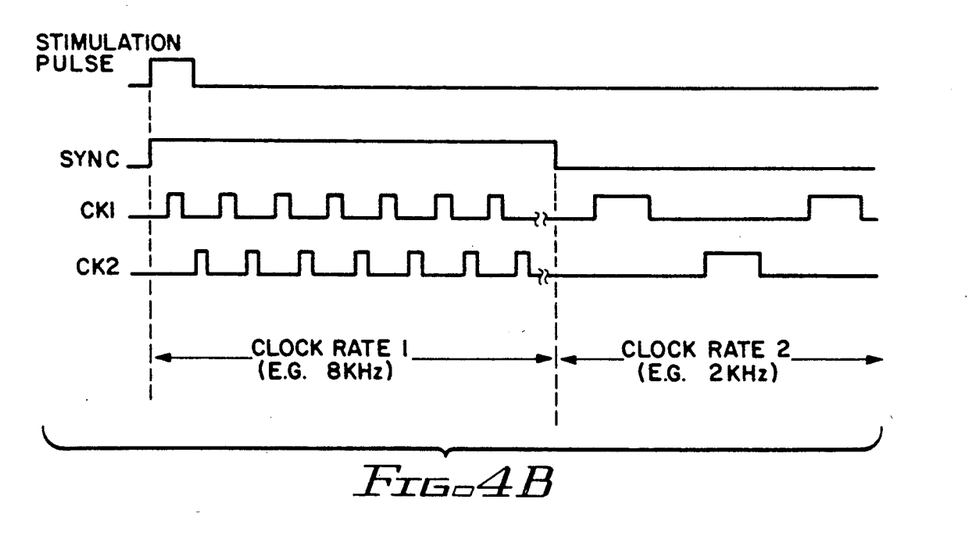
FIG. 4B is a timing diagram of the clock generator circuit of FIG. 4A.

Referring next to FIG. 4A, the clock circuit 120 is shown that is used with the band-pass amplifier 114. An inverting amplifier 36, having feedback, is controlled in its frequency of oscillation by crystal 37. Such frequency might be 32 kHz. Frequency divider 38 provides several outputs, 2, 4, 6, and 8 kHz. Others may be selected, depending on what clock frequencies are desired. The clock frequency may be varied by changing switch 39 to a selected frequency, as selected by an appropriate control signal received over signal line 117 from telemetry control 122. Further, as indicated above, a sync signal may be used with switch 39 in conventional manner in order to synchronize the selection of the clock frequencies with a prescribed event. The clock signals ck 1 and ck 2 are generated as non-overlapping signals as shown by the timing diagram of FIG. 4B. A non-overlap logic circuit 45 comprised of NOR gates 46 and 47 provide ck 1 and ck 2 as non-overlapping clock signals.

It was previously described in connection with FIG. 2A how the clock frequency is involved in the frequency response of the amplifier. This can be used to provide a particularly advantageous feature in a pacemaker. By quadrupling the clock frequency (that is, as shown in FIG. 4A, by throwing switch 39 to 8 kHz), to both the low-pass and high-pass sections, the band-pass characteristics of the sense amplifier are changed in the same ratio. Thus, if the clock frequency is changed at the same time that a stimulation pulse occurs (i.e., as controlled by the sync pulse received over signal line 119, see FIG. 4B), the amplifier is able to recover four times as fast, and is thus ready to sense heart activity in one-fourth the time. This is done by feeding the pacemaker stimulation pulse (or the sync pulse, or another signal synchronized with the pacemaker stimulation pulse) to the control input of switch 39, causing switch 39 to switch the clock frequency, thereby changing the band-pass characteristics, which action improves the recovery time of the amplifier. In contrast, prior art techniques to minimize the recovery time of the input amplifier involved reducing the energy of the pacer pulse coupled to the input amplifier (sense amplifier). Such energy-reducing techniques included limiting the amplitude of the signal, clipping the signal, or actively opening or shorting the input to the amplifier in synchronism with delivery of the pacer pulse.

Figure 9:
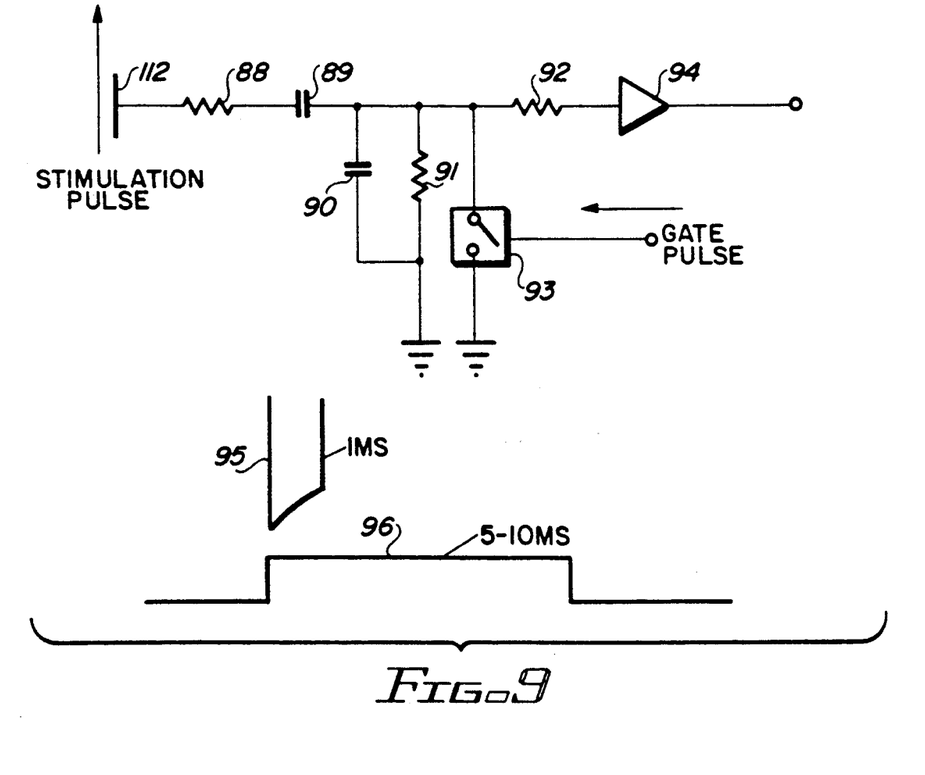
FIG. 9 is an exemplary schematic diagram of the input coupling portion of a sense amplifier, showing how the input coupling is blanked during the generation of a stimulation pulse.

FIG. 9 illustrates an input coupling circuit used with a sense amplifier. The stimulation pulse travels along lead 112 to the heart. The same lead 112 is a sensing lead connected through a high impedance 88, 89, and 92 to the sense amplifier 94. A parallel capacitor 90 and resistor 91 are connected to ground. When a 1 ms stimulation pulse 95 appears on lead 112, a longer, synchronized pulse 96 (5 to 10 mx) is used at gate 93 to connect the input of amplifier 94 to ground. The gate pulse 96 is long enough to allow the circuit to "settle down" and assume a steady state.

Other known techniques may also be used in combination with the novel techniques taught herein in order to prevent unwanted, large signals from entering the band-pass amplifier. The limiters and clippers used in CMOS receiver circuits would be well-adapted to such use, placed at the beginning or early in the pacemaker sensing circuitry. One such circuit is illustrated in "The Radio Amateur's Handbook", pages 8-26, 1982 Edition, published by the American Radio Relay League. Other methods of noise blanking or silencing, or squelch might also be used.

Figure 6:
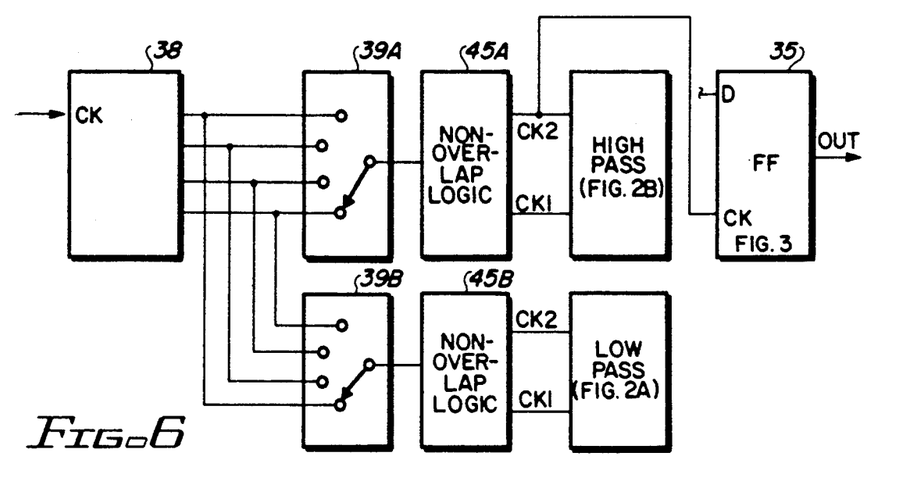
FIG. 6 is a block diagram showing the independent clocking of the low-pass and high-pass sections of the band-pass amplifier.

Referring next to FIG. 6, the band-pass characteristics of the sense amplifier 114 could also be varied by changing the clock frequency to the low-pass and high-pass sections independently of each other. As an example, frequency divider 38 is connected to a non-overlap logic circuit 45A which, in turn, is connected to the high-pass filter section of FIG. 2B. Output flip-flop 35 (shown in FIG. 3, as well as in FIG. 6) obtains its clock signal from the input to high-pass filter section. Likewise, frequency divider 38 is connected to a non-overlap logic circuit 45B which, in turn, is connected to the low-pass filter section of FIG. 2A. In this manner, the high-pass and low-pass sections of the filter may be separately varied through separately setting their clock rates. Thus, the low-pass or the high-pass end of the amplifier may be individually adjusted.

As shown in FIG. 6, D flip-flop 35 may also be clocked at a different frequency, which must, of course, be at a frequency and phase that permits everything in the system to "settle down" before the D flip-flop "reads", or provides an output, based on the various states in the system. As shown, the high-pass section of FIG. 2B may be switched at either a higher or lower frequency than the low-pass section of FIG. 2A, or at the same frequency.

Figure 5:
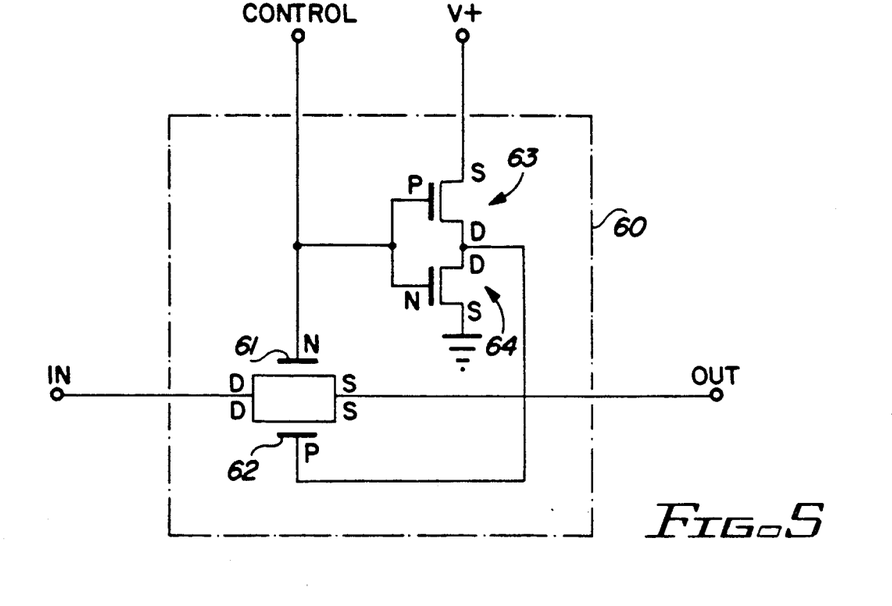
FIG. 5 is a schematic diagram of an electronic switch suitable for use throughout the band-pass amplifier.

FIG. 5 is a schematic diagram of an electronic switch suitable for use in the band-pass sense amplifier 114 of the present invention. A control signal (ck 1) entering the switch 3A, such as shown in FIG. 2A, for example, acts to create low impedance between the in and the out terminals (switch closed) or high impedance between such terminals (switch open). Such impedances are low and high enough to be essentially an open switch or a closed switch, respectively. Such switch 60 is illustrated in FIG. 5 as a CMOS type having complementary transistors 61 and 62 with their drains and sources connected together. Both transistors conduct or neither conducts. Transistors 63 and 64 serve as drivers to aid in changing from conduction to non-conduction and vice-versa. The switch 60 (FIG. 5) can be used to realize the switches shown as boxes (e.g., 3A, 3B, 4A, 4B, 10, 11, 12, 14, 18, 23, and other "boxes" to WhiCh ck 1 and ck 2 signals are directed) in FIGS. 2A and 2B.

Figure 7:
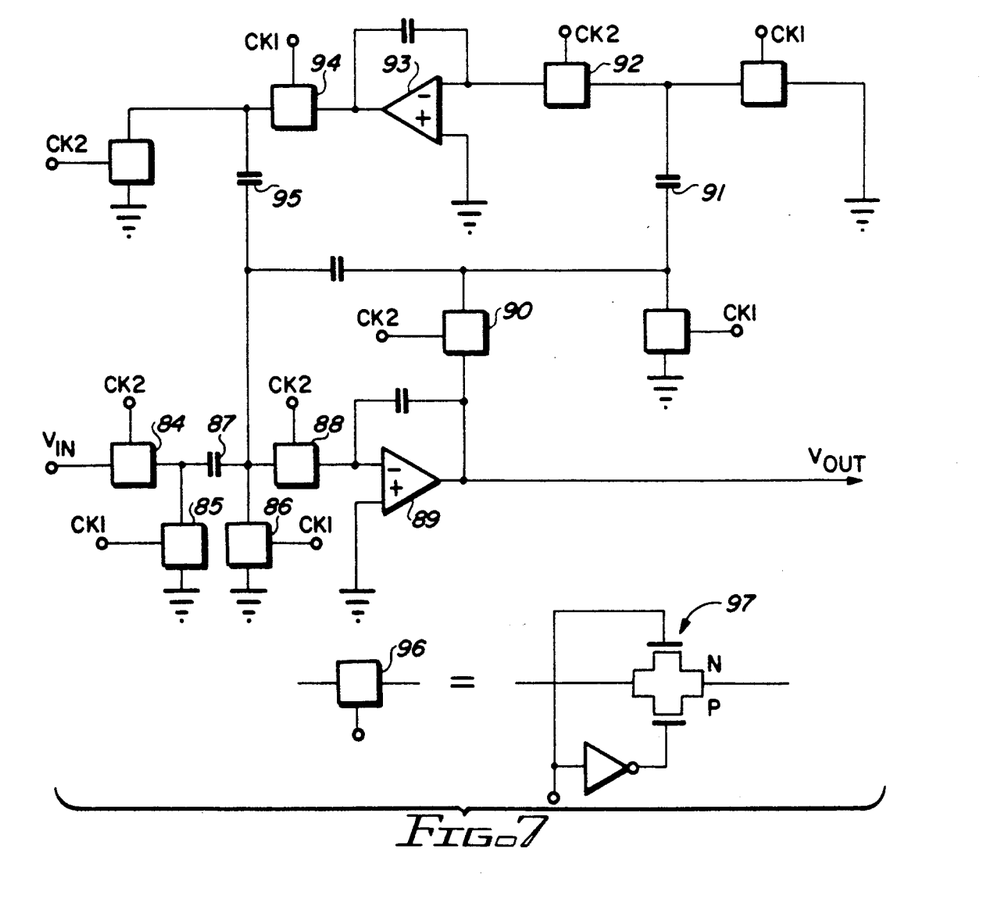
FIG. 7 is a schematic diagram of a band-pass sense amplifier embodiment using switched capacitors and having second order filtering (which embodiment may be inserted, for example, as a band-pass section within the circuits of Figs. 2A and 2B)

FIG. 7 is a schematic diagram of a second order band-pass filter which may be inserted as a section between the circuits of FIGS. 2A and 2B, or inserted in place of operational amplifier 20 of FIG. 2A (and its associated circuitry) and operational amplifier 24 of FIG. 2B (and its associated circuitry). In general, the circuit of FIG. 7 operates by switches 84 and 88 (controlled by ck 2), transferring the charge on capacitor 87 to the input of amplifier 89. Switches 85 and 86 (controlled by ck 1) discharge capacitor 87 between transfer cycles. Switch 90, capacitor 91, and switch 92 similarly transfer the output from amplifier 89 to the input of feedback amplifier 93. Amplifier 93, in turn, charges capacitor 95, capacitor 95 is fed back to the input of amplifier 89. The electronic switches illustrated as blocks, such as 96 in FIG. 7 (and in other Figures of the drawings), may be implemented as shown at 97 by an N-type and a P-type transistor. The circuit of FIG. 5 may also be used to perform this switching function. The band-pass amplifier of FIG. 7 is more fully described in the IEEE Transactions on Circuits and Systems, Vol. CAS-27, No. 4, April 1980, in an article entitled, "Improved Circuits for the Realization of Switched-Capacitor Filters".

Figure 8:
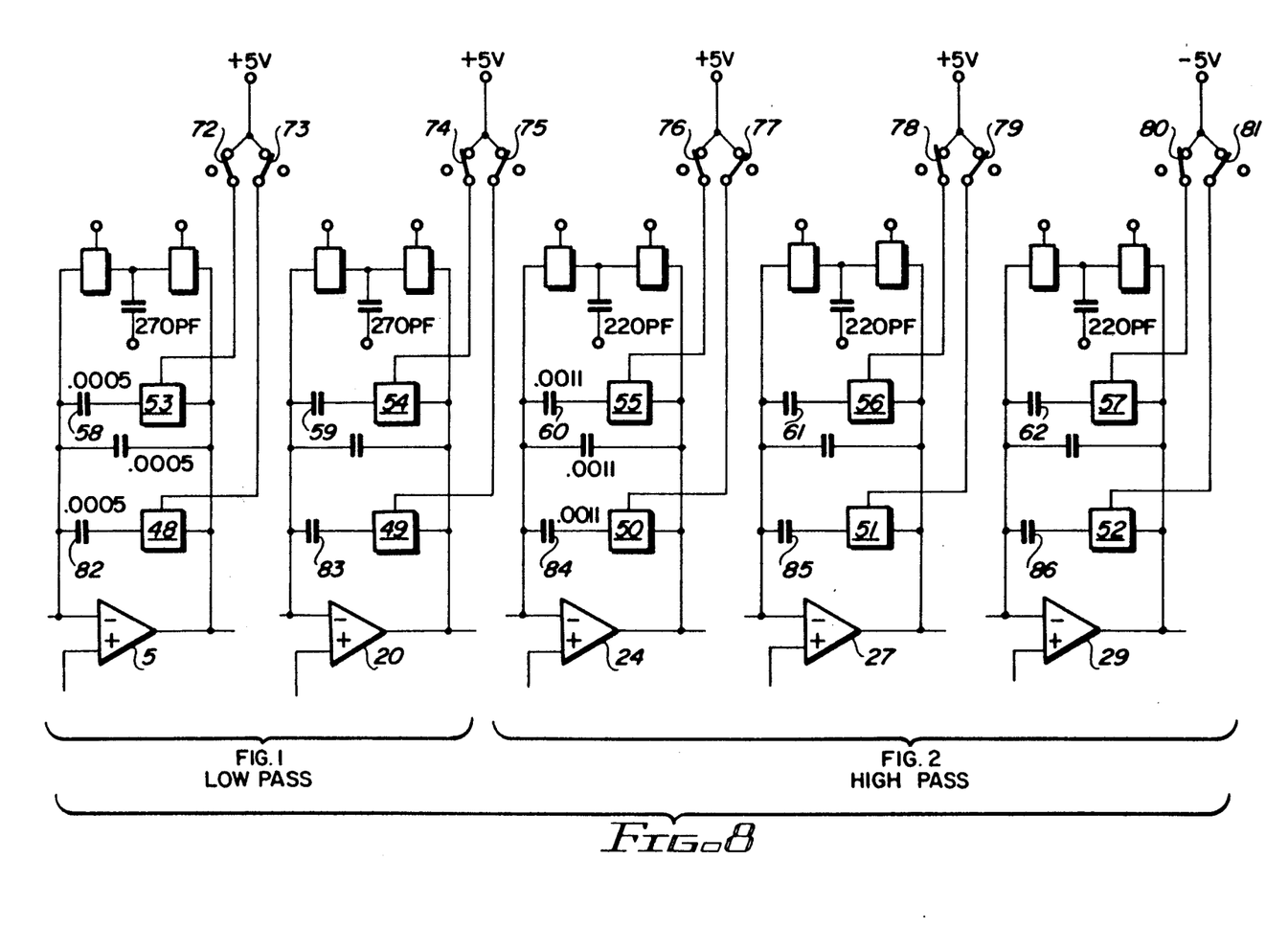
FIG. 8 is a schematic diagram that illustrates how the band-pass frequency can be changed up or down by switching different capacitors into the circuit, as distinguished from switching the clock frequency as is done in FIGS. 2A and 2B.

FIG. 8 shows an embodiment of the invention wherein the frequency of the band-pass amplifier might be varied by switching capacitors, as well as by changing the clock frequency. Switches 48 to 57 may be driven, or controlled, by other switches 72 to 81, flip-flops, electronic switches or control bus information, or other means. Switches 48 to 57, in turn, connect capacitors 58 to 62 and 82 to 86 into the feedback circuit of each of the amplifiers 5, 20, 24, 27, and 29. The feedback capacitors in the low-pass section (for amplifiers 5 and 20 of FIG. 1) are, in this FIG. 8 embodiment, 0.0005 microfarads. The feedback capacitors in the high-pass section (for amplifiers 24, 27, and 29 of FIG. 2B) are, in this FIG. 8 embodiment, 0.0011 microfarads. Thus, the band-pass frequency of the amplifier system, or its high-pass or its low-pass, may be changed up or down by means other than changing clock frequency.

Inasmuch as the gain or the band-pass frequency, or both, of the subject invention amplifier are programmable by electric signals, the amplifier is particularly useful in pacemakers which are programmable by remote means, such as telemetry or other transmission. (See FIG. 1.) In such situations, it is readily understood that the amplifier may be remotely programmed by reason of its programmability.

Although particular embodiments of the invention have been described and illustrated, it is to be clearly understood that the same is by wa of illustration and example only, and is not to be taken by way of limitation, the spirit and scope of this invention being limited only by the terms of the appended claims.

What is claimed is:

1. A programmable implantable medical device comprising:

a pacemaker for generating stimulation pulses;

a pair of electrodes coupled to the pacemaker for sensing electrical signals developed therebetween and for delivering said stimulation pulses to a desired location;

programmable band-pass amplifier means coupled to said electrodes for sensing and processing electrical signals, said programmable band-pass amplifier means including:

an amplifier having an input terminal and an output terminal, said electrical signals sensed by said electrodes being applied to said input terminal, said amplifier causing said electrical signals to be amplified by a desired gain factor and presented at the output terminal of said amplifier, capacitor means for coupling to the amplifier, switching means for switchably coupling said capacitor means to said amplifier, said switching means limiting the electrical signals amplified by said gain factor to those electrical signals having a frequency that falls within a band of frequencies bounded by a lower cut-off frequency and an upper cut-off frequency, the upper and lower cut-off frequencies of said frequency band being controlled by the rate at which said capacitor means is switchably coupled to said amplifier by said switching means, said switching rate, in turn, being controlled by a clock signal applied to said switching means; and clock signal generating means coupled to said switching means for generating said clock signal at one of a plurality of possible clock frequencies, said clock signal generating means responsive to a remotely telemetered signal for selecting one of the plurality of possible clock frequencies for controlling the rate at which said capacitor means is switchably coupled to said amplifier;

whereby the frequency band of said band-pass amplifier means can be changed to a desired value by remotely changing the frequency of the clock signal generated by said clock signal generating means.

2. The implantable medical device of claim 1 wherein said clock signal generating means includes means for changing the frequency of said clock signal simultaneously with the delivery of said stimulation pulses.

3. The implantable medical device of claim 1 wherein said capacitor means comprises a plurality of capacitors, said clock signal comprising a first clock signal and a second clock signal, said switching means comprising first switch means for switchably connecting a first of said plurality of capacitors to the input terminal of said amplifier in response to the first clock signal, and second switch means for switchably connecting a second of said plurality of capacitors to the output terminal of said amplifier in response to the second clock signal.

4. The implantable medical device of claim 3 wherein said clock signal generating means generates said first and second clock signals at the clock signal frequency but at a different phase, whereby the operation of said first and second switch means does not occur at the same time, but occurs in a sequence defined by the phase relationship of said first and second clock signals.

5. The implantable medical device of claim 1 wherein said amplifier comprises a first amplifier stage for setting one of the upper or lower cut-off frequencies of said frequency band, and a second amplifier stage for setting the other of the upper or lower cut-off frequencies of said frequency band, and wherein said capacitor means comprises a first stage capacitor and a second stage capacitor, and further wherein said first stage capacitor is switchably coupled to said first amplifier stage by said switching means, and said second stage capacitor is switchably coupled to said second amplifier stage by said switching means.

6. The implantable medical device of claim 1 including telemetry means for receiving a remotely telemetered signal and for generating a gain control signal in response to such remotely telemetered signal, and wherein said switching means includes gain switch means responsive to said gain control signal for selectively adjusting the gain factor of said amplifier.

7. A sensing amplifier for use in an implantable medical device, said implantable medical device generating prescribed event signals and including a pair of electrodes between which said prescribed event signals are carried and between which an electrical signal having a broad frequency spectrum may be developed, said sensing amplifier comprising:

means for coupling the pair of electrodes to the sensing amplifier;

a first capacitor;

first amplifier means coupled to said pair of electrodes for amplifying selected frequency components of the electrical signal developed between said pair of electrodes, said selected frequency components comprising those components of said electrical signal having a frequency less than a first specified frequency, said first specified frequency being determined by the rate at which said firsts capacitor is switchably connected to said first amplifier means;

clock generating means for generating first and second clock signals;

first switching means responsive to said first clock signal for switchably connecting said first capacitor to said first amplifier means at a first switching rate derived from said first clock signal, whereby said first clock signal comprises a first control parameter that defines said first specified frequency;

a second capacitor;

second amplifier means coupled to said pair of electrodes, said selected frequency components comprising those components of said electrical signal having a frequency greater than a second specified frequency, said second specified frequency being determined by the rate at which said second capacitor is switchably connected to said second amplifier means;

second switching means responsive to said second clock signal for switchably connecting said second capacitor to said second amplifier means at a second switching rate derived from said second clock signal, whereby said second clock signal comprises a second control parameter that defines said second specified frequency; and means for serially connecting said first and second amplifier means, whereby only those frequency components of the electrical signal developed between said pair of electrodes above said second specified frequency and below said first specified frequency are amplified by the serial combination of said first and second amplifier.

8. The sensing amplifier of claim 7 wherein said first amplifier means includes a first stage having an input and an output and a second stage having an input and an output, each of said stages having a respective capacitor that is switchably connected between the output and input of the respective stage thereof at the first switching rate, said first amplifier means further including a plurality of gain capacitors that can be selectively connected within said first amplifier means in order to change the gain thereof.

9. The sensing amplifier of claim 7 further including threshold generating means for generating a high threshold level signal and low threshold voltage signal; and comparison means coupled to the output of threshold generating means and said serial combination of said first and second amplifier means for generating a data output signal transition from a first voltage level to a second voltage level only when an output analog signal from the serial combination of the first and second amplifier means exceeds said high threshold level signal, and for generating a data output transition from the second voltage level to the first voltage level only when the output analog signal is less than said low threshold level signal.

10. The sensing amplifier of claim 7 further including synchronous switching means coupled to said clock generating means for switching the rates of said first and second clock signals simultaneously with a prescribed event signal generated within said implantable medical device, whereby the specified first and second frequencies of said sensing amplifier are changed upon the occurrence of said prescribed event signal.

11. The sensing amplifier of claim 10 wherein said implantable medical device comprises a pacemaker having means for delivering a stimulation pulse through said pair of electrodes, and further wherein said prescribed event comprises the delivery of the stimulation pulse by said pacemaker, whereby said synchronous switching means switches the specified first and second frequencies of said sensing amplifier at approximately the same time as a stimulation pulse is delivered by said stimulation pulse delivery means.

12. The sensing amplifier claim 11 further including blanking means coupled to said sensing amplifier for preventing electrical signals developed between said pair of electrodes from being coupled to said sensing amplifier for a prescribed time period subsequent to the delivery of said stimulation pulse by said stimulation pulse delivery means.

13. A programmable implantable medical device comprising:

a pair of electrodes for sensing signals developed therebetween and delivering simulation pulses generated by said implantable medical device;

amplifier means coupled to said electrodes for sensing and processing said developed signals, said amplifier means comprising:

a plurality of capacitors, a first amplifier circuit, first switching means responsive to a first select signal for connecting desired combinations of said plurality of capacitors to said first amplifier circuit, second switching means responsive to a clock signal for connecting at least one of said plurality of capacitors to said first amplifier circuit at a frequency determined by said clock signal, and said first amplifier circuit having a gain factor that is controlled by the particular combination of capacitors that are connected thereto by said first switching means, and a band-pass characteristic that is a function of the frequency at which said second switching means connects and disconnects said at least one of said plurality of capacitors thereto;

clock signal generating means for generating said clock signal at a frequency determined by a second select signal; and telemetry means for receiving a remotely telemetered command signal and for selectively generating said first and second select signals in response to a received remotely telemetered command signal, whereby the gain and band-pass characteristics of said amplifier within said implantable medical device can be remotely selected.

14. The programmable implantable medical device of claim 13 wherein said medical device comprises a pacemaker having means for generating a simulation pulse, and wherein said clock signal generating means includes selection means coupled to said stimulation pulse generating means for selecting a first frequency for said clock signal simultaneously with the generation of the stimulation pulse, and for selecting a second frequency for said clock signal a prescribed time after the generation of the simulation pulse.

* * * * *